US011191890B2

(12) United States Patent
Chassot et al.

(10) Patent No.: US 11,191,890 B2
(45) Date of Patent: Dec. 7, 2021

(54) INJECTION SYSTEM AND PATIENT SET ASSEMBLY THEREFOR

(71) Applicant: ACIST MEDICAL SYSTEMS INC., Eden Prairie, MN (US)

(72) Inventors: Pierre-Yves Chassot, Thoiry (FR); Jens Warming, Renens (CH)

(73) Assignee: ACIST MEDICAL SYSTEMS INC., Eden Prairie, MN (US)

(*) Notice: Subject to any disclaimer, the term of this patent is extended or adjusted under 35 U.S.C. 154(b) by 0 days.

(21) Appl. No.: 17/260,632

(22) PCT Filed: Jul. 15, 2019

(86) PCT No.: PCT/EP2019/068988
§ 371 (c)(1),
(2) Date: Jan. 15, 2021

(87) PCT Pub. No.: WO2020/016172
PCT Pub. Date: Jan. 23, 2020

(65) Prior Publication Data
US 2021/0244877 A1  Aug. 12, 2021

(30) Foreign Application Priority Data
Jul. 17, 2018 (EP) .................................... 18183892

(51) Int. Cl.
*A61M 5/142* (2006.01)
*A61M 5/14* (2006.01)
(Continued)

(52) U.S. Cl.
CPC .......... *A61M 5/14232* (2013.01); *A61M 5/14* (2013.01); *A61M 5/142* (2013.01);
(Continued)

(58) Field of Classification Search
CPC .............. A61M 5/145; A61M 5/14244; A61M 5/14248; A61M 5/14232; A61M 5/14;
(Continued)

(56) References Cited

U.S. PATENT DOCUMENTS

| 5,213,483 A | 5/1993 | Flaherty et al. |
| 2006/0173419 A1* | 8/2006 | Malcolm ................. F04B 49/06 604/246 |
| 2014/0039310 A1 | 2/2014 | Suchecki et al. |

FOREIGN PATENT DOCUMENTS

WO    2017137421 A1    8/2017

OTHER PUBLICATIONS

International Search Report and Written Opinion for PCT/EP2019/068988, dated Oct. 4, 2019.

* cited by examiner

*Primary Examiner* — Nathan R Price
*Assistant Examiner* — Anh Bui
(74) *Attorney, Agent, or Firm* — Vivicar Law, PLLC

(57) ABSTRACT

An injection system is proposed which comprises at least one supply station for supplying a medical fluid to be injected into a patient's vasculature, a pressurizing unit comprising a motor for pressurizing said medical fluid, a delivery arrangement in fluid communication with the at least one supply station and a patient set assembly in fluid communication with the delivery arrangement. The patient set assembly comprises a delivery tube for delivering the pressurized fluid to the patient and a peristaltic pump component comprising a casing which includes an inlet port and an exit port, the inlet port being in fluid communication with the delivery arrangement and the exit port being in fluid communication with the delivery tube. According to an embodiment of the present invention, in proximity of the inlet port, the casing of the peristaltic pump component has (Continued)

a substantially U-shaped configuration. The present invention also relates to a patient set assembly and to a peristaltic pump component.

18 Claims, 9 Drawing Sheets

(51) Int. Cl.
*A61M 5/145* (2006.01)
*F04B 43/12* (2006.01)
(52) U.S. Cl.
CPC ........ *A61M 5/145* (2013.01); *A61M 5/14244* (2013.01); *A61M 5/14248* (2013.01); *F04B 43/12* (2013.01); *F04B 43/1253* (2013.01); *F04B 43/1261* (2013.01)
(58) Field of Classification Search
CPC ......... A61M 5/142; A61M 2005/14268; F04B 43/1261; F04B 43/1253; F04B 43/12
See application file for complete search history.

PRIOR ART

INJECTION SYSTEM AND PATIENT SET ASSEMBLY THEREFOR

CROSS-REFERENCE TO RELATED APPLICATIONS

This application is the national stage application of corresponding international application number PCT/EP2019/068988, filed Jul. 15, 2019, which claims priority to and the benefit of European application no. 18183892.1, filed Jul. 17, 2018, which is hereby incorporated by reference in its entirety.

TECHNICAL FIELD

The present disclosure relates to the field of medical equipment. More specifically, the present disclosure relates to injection systems of medical fluids. Even more specifically, the present disclosure relates to injection systems provided with disposable patient sets comprising peristaltic pumps.

BACKGROUND ART

The background of the present disclosure is hereinafter introduced with the discussion of techniques relating to its context. However, even when this discussion refers to documents, acts, artifacts and the like, it does not suggest or represent that the discussed techniques are part of the prior art or are common general knowledge in the field relevant to the present disclosure.

The injection of fluids into patients is commonplace in several medical procedures. For example, a contrast agent (or contrast medium) may be injected, possibly along with a saline solution, to enhance contrast of target (body) features (for example, human body's structures or organs) within the patients during scan examinations thereof. Particularly, in imaging applications (wherein a visual representation of the interior of the patients is created in a non-invasive way without turning to surgery techniques) the use of a contrast agent makes the target features more conspicuous. As a result, target features that would otherwise be less distinguishable from other nearby features (for example, surrounding tissues) are advantageously highlighted. This significantly facilitates the task of clinicians in diagnostic applications, and particularly in the identification and/or characterization of lesions, the monitoring of their evolution or the response to medical treatments. For example, a iodine-based contrast agent (such as comprising iopamidol) is commonly used in Computed Tomography (CT) applications (such as angiography investigations).

The contrast agent is usually injected into a blood vessel of a patient by an (automated) injection system. The injection system pressurizes the contrast agent and injects it into the patient's vasculature or organ under predetermined injection conditions, for example at predetermined flow rate and volume. In this way, the contrast agent may be injected in a controlled, safe and efficient manner.

Therefore, an injection system is typically provided with one or more supply stations for supplying the contrast agent and/or the saline solution from a corresponding container (e.g. a bottle, a bag or a pouch). The injection system is further provided with a delivery arrangement that is in fluid communication with the at least one supply station and a pressurizing unit. Since the delivery arrangement is positioned upstream of the pressurizing unit and, therefore, it is not in direct connection with a patient, with substantially no risk or a very low risk of cross-contamination, generally the delivery arrangement is a disposable element that is changed periodically (for example, every 10 or 12 hours). This means that the delivery arrangement is not changed when a new patient undergoes an examination and it is typically kept in place for multiple successive injections, till the predetermined period of time designed for the delivery arrangement is fully elapsed.

The powered injection systems known in the art and presently available on the market are divided into two major groups: syringe injectors (like Empower CTA® or Empower CTA®+ manufactured by Bracco Injeneering SA) and syringe-less injectors (like CT Exprès® manufactured by Bracco Injeneering SA).

The present invention is directed to powered syringe-less injectors where the pressurizing unit comprises a peristaltic pump that houses a plurality of rollers, among which a tube is inserted, and then sequentially and alternately squeezed by the rollers for finally injecting a fluid into a patient (typically the fluid is a medical fluid which is a contrast agent or two different contrast agents, a saline solution, a contrast agent and a saline solution mixture, or a medication).

Some specific medical procedures require that the powered injectors provide for particularly demanding hydraulic performances, in particular in terms of pressure and flow rate of the fluid to be injected into a patient. This aspect is particularly critical for syringe-less injectors since, due to their intrinsic design characteristics, they can hardly compete with syringe injectors and provide high pressure and flow rate values.

For example, it is becoming more and more frequent that a powered injector is requested to be connected to insertable devices (e.g. PICC & PORT) which are already implanted in a patient's vasculature and which are used for establishing an intravascular access to a patient.

PICC is a Peripherally Inserted Central Catheter that is typically placed in a patient's arm to allow for a prolonged intravenous access, such as for extended antibiotic treatment or chemotherapy. A PICC is inserted in a peripheral vein (e.g. the cephalic vein, the basilic vein or the brachial vein) and then advanced through increasingly larger veins towards the heart, until the catheter tip rests in the distal superior vena cava or cave-atrial junction while the proximal end of the PICC remains outside of the body. A PICC is typically left in place in the patient's arm for periods ranging from six weeks to one year.

A PORT usually comprises a reservoir (the portal)—that is provided with a septum for needle insertion—and a catheter that goes from the reservoir into a patient's vein. The reservoir is surgically inserted under the skin in the upper chest or in the arm, and the catheter is fully inserted into the vein, i.e. there's no catheter tail outside of the patient's body.

Some patients that need to undergo an imaging examination (e.g. a computed tomography—CT) may already have a PICC in place for other purposes. Therefore, existing multi-lumen PICCs may be used for power injection of diagnostic and/or therapeutic agents. However, the presence of said insertable devices represents a considerable technical constraint for a powered injector (especially for a powered syringe-less injector) that is requested to generate pressure and flow rate values sufficiently high in order to still guarantee the desired and predetermined injection performances, even when such insertable devices are interposed between the injection system and the patient.

The Applicant has thus perceived the need of improving the hydraulic performance of a powered syringe-less injector so that a predetermined injection procedure is not affected by any additional medical device (e.g. PICC & PORT) already inserted in a patient's body and to which the syringe-less injector is requested to be connected.

In detail, the Applicant has perceived the need of improving the fluid flow within the peristaltic pump of a powered syringe-less injection system in order to reduce most of, if not all, the structural constraints that can negatively impact on the overall performance of the injection system, mainly in terms of maximum pressure and maximum flow rate of the injected fluid.

Moreover, the Applicant has also perceived the need of providing an injection system comprising a spike connector which promotes a correct and homogeneous fluid flow through the spike, and which guarantees a gradual and efficient penetration of the spike into a septum (membrane) possessed, for instance, by a delivery arrangement (day set) of said injection system.

SUMMARY

A simplified summary of the present disclosure is herein presented in order to provide a basic understanding thereof; however, the sole purpose of this summary is to introduce some concepts of the disclosure in a simplified form as a prelude to its following more detailed description, and it is not to be interpreted as an identification of its key elements nor as a delineation of its scope.

In order to improve the hydraulic performance of a syringe-less injection system, the Applicant has perceived the need of optimizing the path of the fluid flowing into a patient set assembly of the injection system.

Therefore, according to one aspect of the present disclosure, the Applicant has found that a fluid path optimization can be achieved by suitably designing the connection interface between the patient set assembly and a pressurizing unit of the injection system. In detail, the Applicant has found to provide the casing of a peristaltic pump component of the patient set assembly with a substantially U-shaped configuration in proximity of the peristaltic pump component inlet port so that a substantially straight fluid flow at said connection interface can be obtained, as it will be explained more in detail in the following with reference to the enclosed Figures. In other words, the Applicant has found to change the 90° bending configuration of the prior art into a 180° bending configuration with a large radius, said solution providing a decrease in the total pressure drop within the patient set assembly.

According to a further aspect of the present disclosure, the Applicant has found that the hydraulic performance of the syringe-less injection system can be further improved also by suitably choosing the material of the peristaltic tube on which the peristaltic pump component acts during operation of the syringe-less injection system.

According to a further aspect of the present disclosure, the Applicant has found that the hydraulic performance of the syringe-less injection system can be further improved also by suitably choosing the internal diameter of the delivery tube exiting the patient set assembly with respect to the internal diameter of the peristaltic tube positioned among the rollers of the peristaltic pump component.

Therefore, an aspect of the present disclosure provides for an injection system comprising a peristaltic pump component whose casing, in proximity of the inlet port that fluidically connects the patient set assembly with a delivery arrangement of the injection system, has a substantially U-shaped configuration.

In detail, an aspect of the present disclosure provides for an injection system comprising:
- at least one supply station for supplying a fluid to be injected into a patient's vasculature;
- a pressurizing unit comprising a motor for pressurizing the fluid received from said at least one supply station;
- a delivery arrangement in fluid communication with said at least one supply station;
- a patient set assembly in fluid communication with said delivery arrangement, said patient set assembly comprising:
  - a delivery tube for delivering the pressurized fluid to the patient, and
  - a peristaltic pump component comprising a casing which includes an inlet port and an exit port, the inlet port being in fluid communication with the delivery arrangement and the exit port being in fluid communication with the delivery tube, characterized in that, in proximity of said inlet port, the casing of the peristaltic pump component has a substantially U-shaped configuration.

Moreover, the present disclosure also relates to a patient set assembly for delivering a pressurized fluid to a patient, the patient set assembly comprising:
- a delivery tube in fluid communication with the patient, and
- a peristaltic pump component comprising:
- a casing comprising an inlet port and an exit port, the inlet port being in fluid communication with a delivery arrangement of an injection system and the exit port being in fluid communication with the delivery tube;
- an inlet connector for connecting said peristaltic pump component to a connector of the delivery arrangement, said inlet connector being arranged at said inlet port, and
- at least a couple of rollers for engaging a peristaltic tube in fluid communication with said inlet connector and for pressurizing the fluid flowing into the peristaltic tube when the peristaltic pump component is connected to a pressurizing unit of the injection system and the pressurizing unit is operating, characterized in that, in proximity of said inlet port, the casing of the peristaltic pump component has a substantially U-shaped configuration.

Furthermore, the present disclosure also relates to a peristaltic pump component for delivering a pressurized fluid comprising:
- a casing comprising an inlet port and an exit port;
- an inlet connector for connecting said peristaltic pump component to a delivery arrangement of an injection system, said inlet connector being arranged at said inlet port, and
- at least a couple of rollers for engaging a peristaltic tube in fluid communication with said inlet connector and for pressurizing the fluid flowing into the peristaltic tube when the peristaltic pump component is connected to a pressurizing unit of the injection system and the pressurizing unit is operated, characterized in that, in proximity of said inlet port, the casing of the peristaltic pump component has a substantially U-shaped configuration.

Finally, according to a further aspect the present disclosure relates to an injection system comprising:

at least one supply station for supplying a fluid to be injected into a patient's vasculature;

a pressurizing unit comprising a motor for pressurizing the fluid received from said at least one supply station;

a delivery arrangement in fluid communication with said at least one supply station;

a patient set assembly in fluid communication with said delivery arrangement, said patient set assembly comprising:

a delivery tube for delivering the pressurized fluid to the patient, and a peristaltic pump component comprising an inlet port and an exit port, the inlet port being in fluid communication with the delivery arrangement and the exit port being in fluid communication with the delivery tube, characterized in that said injection system further comprises at least one inlet connector having a spike, said spike comprising:

a cylindrical hollow shaft defining an internal fluid passage;

a substantially rounded, cone-shaped portion provided at the distal end of said shaft, said portion terminating in a substantially rounded and solid tip, and a plurality of elongated inlet openings which partially extend along said shaft and said substantially rounded, cone-shaped portion, said elongated openings being in fluid communication with said internal fluid passage.

According to one embodiment the delivery arrangement of the injection system comprises at least one inlet connector.

According to one embodiment the patient set assembly of the injection system comprises at least one inlet connector.

According to one embodiment the elongated inlet openings have a substantially rectangular shape.

According to one embodiment the elongated inlet openings have a longitudinal extension that is substantially parallel to a spike longitudinal axis.

According to one embodiment the elongated inlet openings are equally distanced from each other along the lateral surface of the cylindrical hollow shaft.

More specifically, one or more aspects of the present disclosure are set out in the independent claims and advantageous features thereof are set out in the dependent claims, with the wording of all the claims that is herein incorporated verbatim by reference (with any advantageous feature provided with reference to any specific aspect that applies mutatis mutandis to every other aspect).

BRIEF DESCRIPTION OF THE DRAWINGS

The solution of the present disclosure, as well as further features and the advantages thereof, will be best understood with reference to the following detailed description thereof, given purely by way of a non-restrictive indication, to be read in conjunction with the accompanying drawings (wherein, for the sake of simplicity, corresponding elements are denoted with equal or similar references and their explanation is not repeated, and the name of each entity is generally used to denote both its type and its attributes, such as value, content and representation). In this respect, it is expressly intended that the figures are not necessary drawn to scale (with some details that may be exaggerated and/or simplified) and that, unless otherwise indicated, they are merely used to illustrate the structures and procedures described herein conceptually. Particularly.

DETAILED DESCRIPTION

Figure 1:
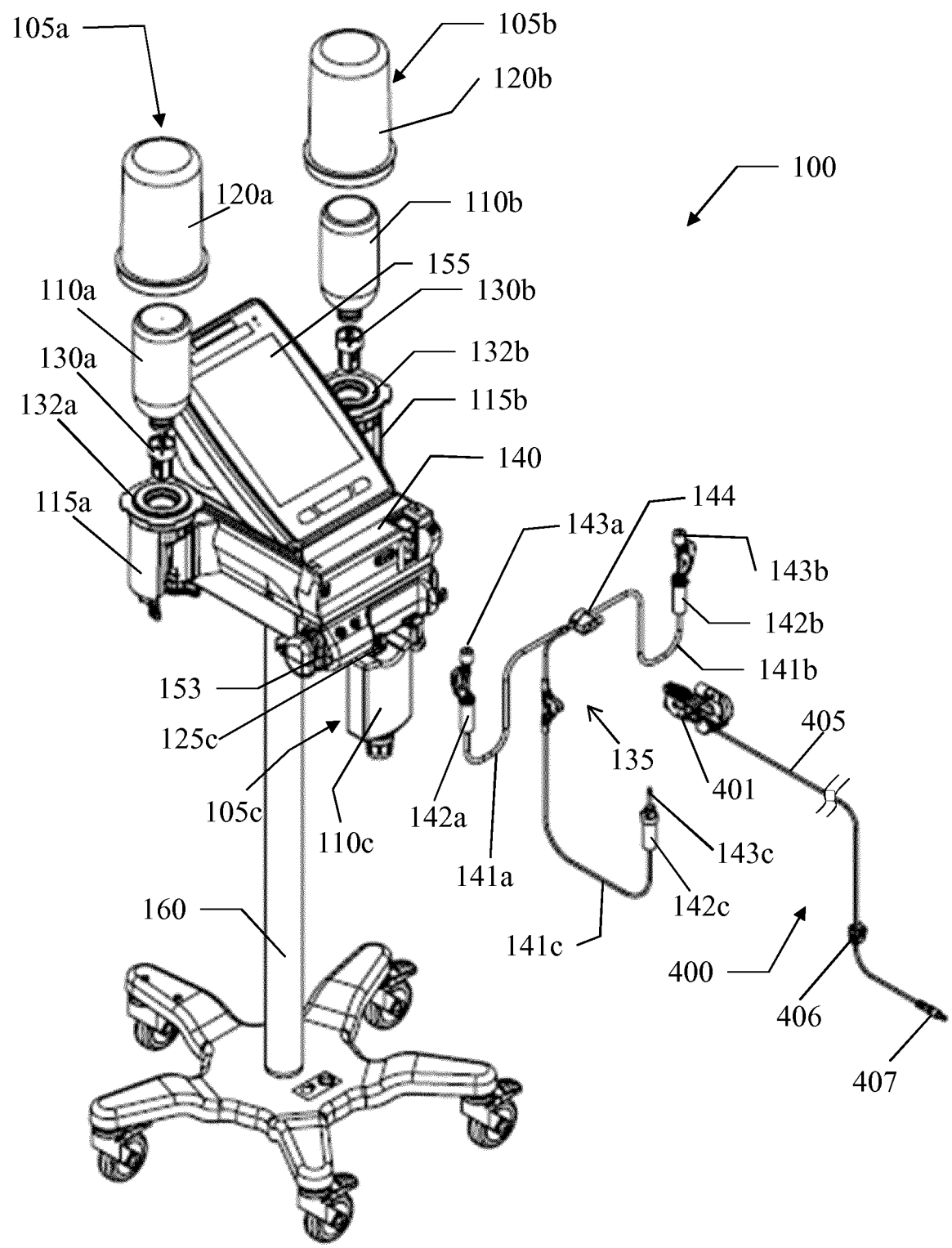
FIG. 1 shows a pictorial representation in partially exploded perspective view of an injection system wherein the solution according to an embodiment of the present disclosure may be applied.

With reference in particular to FIG. 1, a pictorial representation in partially exploded perspective view is shown of an injection system 100 wherein the solution according to an embodiment of the present disclosure may be applied.

The injection system 100 is used to inject one or more fluids into a patient (not shown in the figure). Particularly, the injection system 100 is an automated (powered) syringeless injector that is used by clinicians to inject contrast agent and saline solution during scan examinations (for example, in radiography applications like CT scans).

The injection system 100 shown in FIG. 1 comprises a first supply station 105a, a second supply station 105b and a third supply station 105c for supplying the fluids to be injected from corresponding receptacles. Particularly, the supply station 105a and the supply station 105b supply a fluid from a bottle 110a and from a bottle 110b, respectively (i.e., a container made from glass or rigid plastic). On the contrary, the supply station 105c supplies a fluid from a pouch 110c (i.e., a container made from soft plastic). The supply stations 105a, 105b may be used to supply one or more contrast agents (to enhance contrast of specific body features within the patient), or a contrast agent and a saline solution (comprising a physiological or isotonic solution) respectively, whereas the supply station 105c may typically be used to supply a saline solution. For example, in CT applications the contrast agent may be a iodine-based contrast agent comprising diatrizoate, ioxaglate, iopamidol, iohexol, ioxilan, iopromide or iodixanol, and the saline solution may be sodium chloride. An example of a commercial contrast agent comprising iopamidol is ISOVUE®, manufactured by Bracco Diagnostics Inc. (trademarks). Each bottle 110a, 110b may contain a single or multiple dose (for example, 50-500 ml) of different contrast agents (a first contrast agent in the first bottle and a second different contrast agent in the second bottle, the two contrast agents to be supplied according to a predetermined sequence) or of the same contrast agent (to be supplied in succession to increase the duration of the scan examination). The pouch 110c generally contains a bulk of saline (for example, 100-1,000 ml) to be supplied before (pre-flush), after (post-flush) or between (interphase) injections of the contrast agent, or alternatively in rapid alternate succession with the contrast agent (to achieve a mixing of the contrast agent and the saline solution within an organ of the patient, for example within the heart). Alternatively, as mentioned above, the supply stations 105a and 105b may be used to supply a contrast agent and a saline solution, respectively. In this latter case the supply station 105c can be eliminated.

More specifically, each supply station 105a, 105b (respectively) comprises a bottle holder 115a, 115b for housing and supporting the bottle 110a, 110b. A protective cover 120a, 120b may be mounted on the bottle holder 115a, 115b to cover the bottle 110a, 110b when it is held thereon, thereby defining a (closed) chamber for housing the bottle 110a, 110b. The bottle holder 115a, 115b and the protective cover 120a, 120b protect the bottle 110a, 110b from external accidental shocks. Moreover, typically the protective cover 120a, 120b is made of a thermally insulating material (for example, polycarbonate) to reduce heat losses, thereby helping to maintain warm (for example, at about the body temperature) the medical fluid contained in the bottle 110a, 110b, which was previously heated in a dedicated device (not shown) separate from the injection system. Typically the supply station 105c comprises a hook 125c for hanging the pouch 110c.

The injection system further comprises a delivery arrangement 135 which determines a fluid pathway for delivering the medical fluids from the receptacles 110a, 110b, 110c to a pressurizing unit 140. The tubing of the delivery arrangement is made from a plastic material. Preferably the tubing of the delivery arrangement is made from PVC.

For this purpose, in each supply station 105a, 105b a bottle connector 130a, 130b is arranged in a connection port 132a, 132b of the bottle holder 115a, 115b. The bottle connector 130a, 130b comprises a spike for connecting to the bottle 110a, 110b and a connection element (for example, a septum or a male luer lock fitting) in fluid communication with the spike. The spike and the connection element are located at opposite longitudinal ends of the bottle connector 130a, 130b. Typically, the bottle connector 130a, 130b also comprises a filtering unit (not shown in the figure) between its spike and connection element. The bottle connector 130a, 130b is a disposable element for use with a single bottle 110a, 110b (for example, with the spike tip that breaks off and remains inside the bottle 110a, 110b when the bottle connector 130a, 130b is removed in order to prevent any accidental re-use thereof).

The delivery arrangement 135 (which is often indicated by the technicians as "Day Set" or "Transfer Set") connects all the supply stations 105a, 105b, 105c to the pressurizing unit 140 for transferring the corresponding medical fluids from the receptacles 110a, 110b, 110c to a patient set assembly 400 which is received inside the pressurizing unit 140. The delivery arrangement 135 comprises a transfer line for each supply station 105a, 105b, 105c. The transfer line of each supply station 105a, 105b comprises a flexible tubing 141a, 141b that is provided (at a distal end thereof with respect to the pressurizing unit 140) with a reservoir (or drip chamber) 142a, 142b and a connection element 143a, 143b for mating with the connection element of the bottle connector 130a, 130b. For example, the connection element 143a, 143b is a spike connector in case the connection element of the bottle connector 130a, 130b is a septum; alternatively, the connection element 143a, 143b is a female luer lock fitting in case the connection element of the bottle connector 130a, 130b is a male luer lock fitting. During operation of the injection system 100, the reservoir 142a, 142b and the connection element 143a, 143b are arranged inside the bottle holder 115a, 115b. Analogously, the transfer line of the supply station 105c comprises a flexible tubing 141c that is provided (at a distal end thereof with respect to the pressurizing unit 140) with a reservoir (or drip chamber) 142c and a spike 143c for connecting to the pouch 110c. All the flexible tubings 141a, 141b, 141c are coupled (at their proximal ends with respect to the pressurizing unit 140) with a T-connector 144, which comprises a plug for insertion into a corresponding port of the pressurizing unit 140.

The pressurizing unit 140 comprises an electric motor (not visible in the figure) which acts on a peristaltic pump that pressurizes the medical fluids (received from the receptacles 110a, 110b, 110c via the delivery arrangement 135) for their injection into the patient (for example, up to a pressure of 17 bar, or at a flow rate from 0.5 to 9.9 ml/s).

As already mentioned above, the injection system 100 further comprises a patient set assembly 400 which connects the delivery arrangement 135 to the patient for delivering the pressurized fluids thereto. The patient set assembly 400 comprises a delivery tube 405 which is provided (at a proximal end thereof with respect to the pressurizing unit) with a peristaltic pump component 401. The latter is introduced into a dedicated port provided in the pressurizing unit 140 and it is also put in fluid communication with the T-connector 144 of the delivery arrangement 135. The peristaltic pump component 401 houses a rotor having a plurality of squeezing rollers, among which a corresponding portion of a peristaltic tube (not visible in FIG. 1) is inserted, said peristaltic tube being in fluid communication with the delivery tube 405.

When the patient set assembly 400 is of single use type (as shown in FIG. 1) for use by a single patient only, the delivery tube 405 is quite long and it is provided (at a distal end thereof with respect to the pressurizing unit) with a connection element 407 for mating with a respective corresponding connection element (for example, a plug) of a peripheral catheter (not shown) which is inserted through the skin into a peripheral vein of the patient to be treated. The delivery tube 405 can be also provided with a clip 406 that pinches the tube and closes the delivery line during installation or uninstallation of the peripheral catheter.

Figure 2:
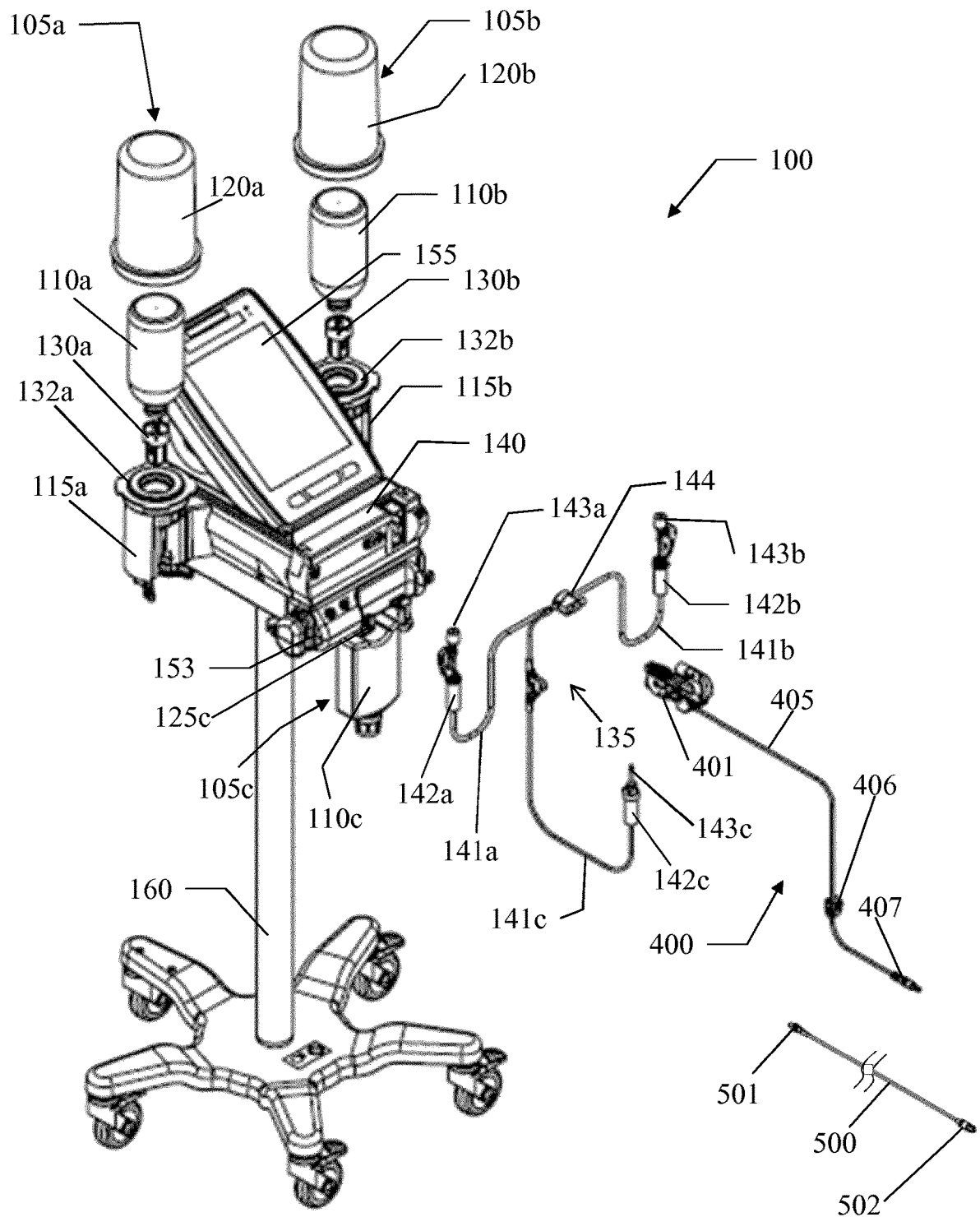
FIG. 2 shows a pictorial representation in partially exploded perspective view of an alternative injection system wherein the solution according to an embodiment of the present disclosure may be applied.

When the patient set assembly 400 is of multiple use type (as shown in FIG. 2) for use with multiple patients, typically the delivery tube 405 (delivery line) is quite short and it is provided at the distal end thereof with a connection element 407 for mating with a corresponding connection element 501 of an additional patient line 500 which typically comprises a quite long flexible tube. The additional patient line 500 terminates (at its distal end) with a connection element 502 for mating with a corresponding connection element possessed by a peripheral catheter (not shown).

The patient set assembly 400 is a disposable element which, in case of single use (see FIG. 1), is for use entirely with a single patient, while, in case of multiple use (see FIG. 2), it is changed periodically (for example, every 12 hours), except for the additional patient line 500 which is intended for use with a single patient only and thus it is discarded at the end of each injection procedure for a given patient, thereby being substituted with a new one when a new patient is ready to be treated.

According to the embodiment of FIG. 1 or FIG. 2, each supply station 105a, 105b, 105c of the injection system 100 further comprises clamping means (not shown in the figures) for engaging the delivery arrangement 135, and thus blocking or unblocking the passage of the fluids flowing there through. Specifically, the clamping means of supply station 105a, 105b is located inside the bottle holder 115a, 115b, while the clamping means of supply station 105c is located in a dedicated seat 153 housed in the front part of the injector body. Activation (i.e. clamping and de-clamping) of the clamping means is controlled automatically by the injector software, i.e. it is part of the injection steps that are carried out by the injector (according to the injection protocols that are loaded on the injector, typically on the injector remote console not shown in the figures).

A control unit 155 controls the operation of the injection system 100. For example, the control unit 155 comprises a (main PCB) board with a microprocessor, a RAM that is used as a working memory by the microprocessor and a flash EPROM that stores information to be preserved even when a power supply is off (particularly, a control program of the injection system 100). Moreover, the control unit 155 comprises a touch-screen and several buttons, which are used by an operator to interact with the control unit 155.

Most commonly the injection system 100 is supported by a stand 160. The stand 160 is provided with wheels to facilitate moving the injection system 100; moreover, the wheels have a foot brake to secure the injection system 100 in position. According to an alternative embodiment (not shown), the injection system is provided with a ceiling mount which allows installation of the injection system in the ceiling of the intervention/scan room.

Figure 3:
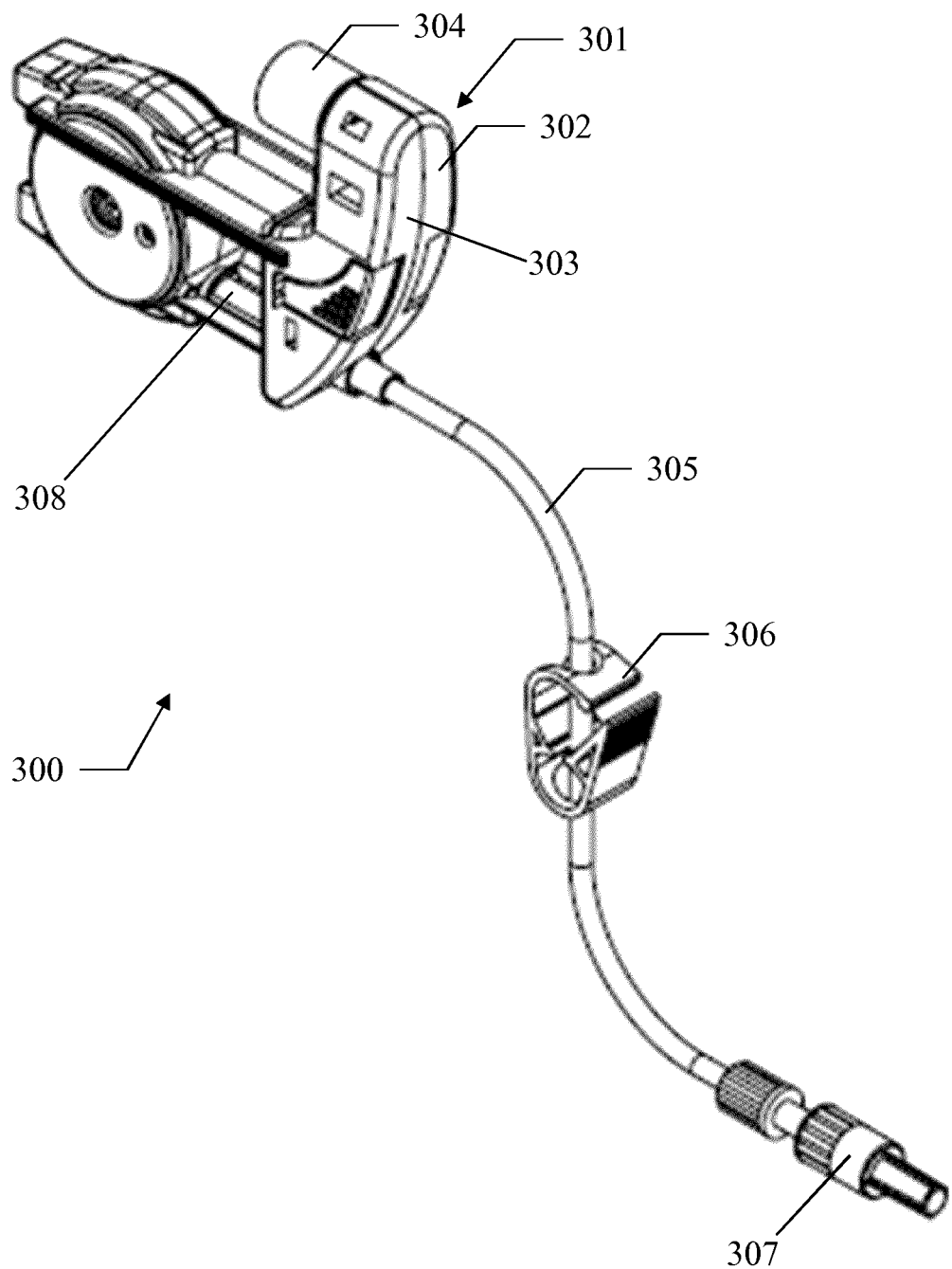
FIG. 3 shows a pictorial perspective view of a current patient set assembly.

FIG. 3 shows a perspective view of a current (prior art) patient set assembly 300 which comprises a peristaltic pump component 301 and a delivery tube 305, the latter being provided at its distal end with a connection element 307 for fluidically communicate with a patient line (not shown) or directly with a peripheral catheter (not shown) inserted within a patient's vein or artery. The delivery tube 305 can also be provided with a clip 306 for pinching the tube and closing the delivery line during positioning of the peripheral catheter.

Figure 4:
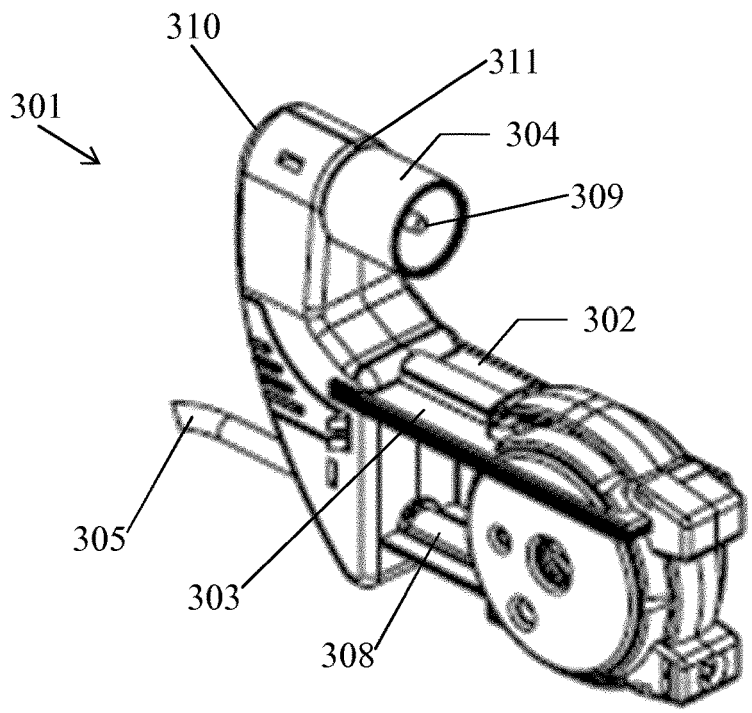
FIG. 4 shows a pictorial perspective view of the current peristaltic pump of the patient set assembly of FIG. 3.
Figure 5:
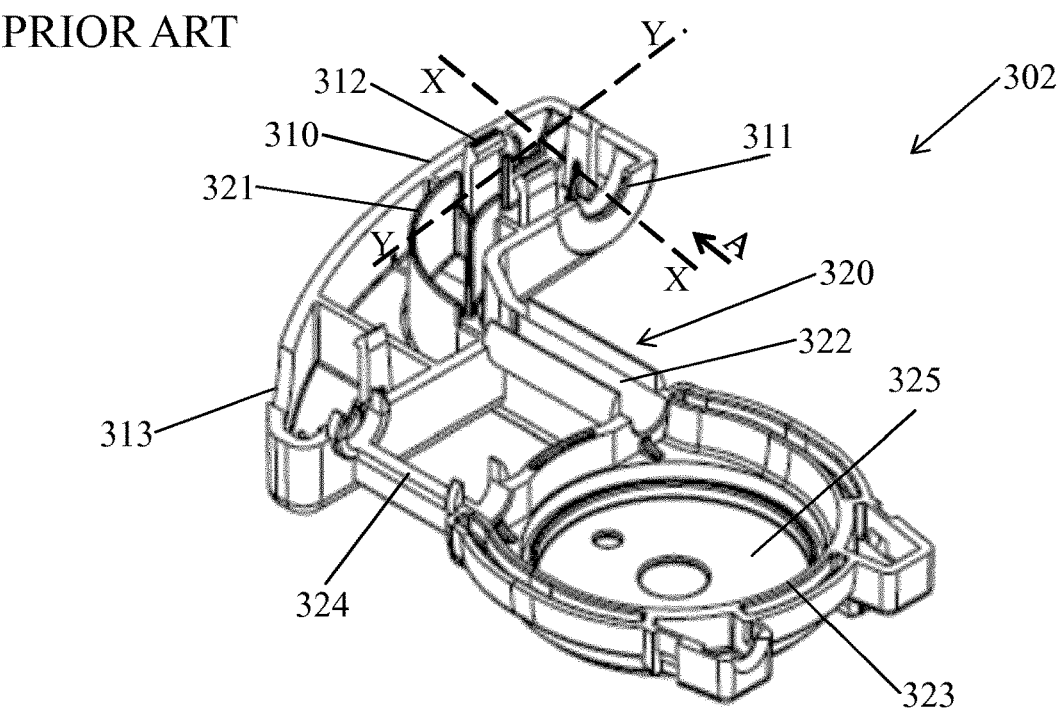
FIG. 5 shows a pictorial perspective view of one half of the casing of the current peristaltic pump of FIG. 4.

As better shown also in FIG. 4 and FIG. 5, the peristaltic pump component 301 comprises two specular mating parts 302, 303 which, once assembled together (e.g. preferably by gluing or by welding), define a closed casing for receiving an inlet connector 304, at least a couple of rollers (not shown) of the peristaltic pump and a guiding path 320 for suitably guiding a peristaltic tube 308 fluidically communicating, respectively, with the inlet connector 304 and the delivery tube 305.

According to the embodiment shown in FIGS. 3 to 5, the inlet connector 304 is a spike connector comprising a spike 309 which, during operation of the injection system 100, penetrates a membrane possessed by the T-connector 144 of the delivery arrangement 135, thereby making the fluid connection between the delivery arrangement 135 and the patient set assembly 400. Alternatively (not shown in the figures), the inlet connector is a spike-less connector, and a safe and fluidic connection with a corresponding connector of a delivery arrangement is performed by any suitable mechanical means (e.g. a bayonet fitting or a snap-fit mechanism). Typically the inlet connector 304 is L-shaped and it is engaged in a protruding portion 310 standing out from the substantially rectangular casing main portion of the peristaltic pump component 301. In more detail, the protruding portion 310 has a substantially rectilinear development in a direction which is substantially perpendicular to a minor lateral surface of the rectangular casing. The inlet connector 304 is located in correspondence of an inlet port 311 of the peristaltic pump component 301 so that the inlet connector proximal end (i.e. the inlet connector portion provided with the spike 309) protrudes away from the inlet port 311. In order to properly and safely engage and retain the inlet connector 304 within the protruding portion 310, clipping members 312 are provided at the distal end of the L-shaped inlet connector 304.

As shown in more detail in FIG. 5, the guiding path 320 comprises a plurality of guiding segments for housing and guiding the peristaltic tube 308 from the inlet connector 304, along the rollers (not shown) of the peristaltic pump component 301 up to the exit port 313 thereof. In FIG. 5 the guiding path 320 is shown only in the first mating part 302 of the peristaltic pump component 301; however, an analogous and symmetric guiding path 320 is provided also in the second mating part 303 of the peristaltic pump component 301 so that, once the two mating parts 302, 303 are assembled together, the overall guiding path 320 defines a predetermined path which substantially encloses the peristaltic tube 308 there into. The guiding path 320 comprises a curved guiding segment 321 which is positioned in the protruding portion 310 and which guides the peristaltic tube 308 in proximity of the distal end of the inlet connector 304. Moving in the direction towards the exit port 313, the guiding path 320 further and successively comprises a first rectilinear guiding segment 322, a curvilinear guiding segment 323 and a second rectilinear guiding segment 324, these segments being all contained in the substantially rectangular main portion of the casing of the peristaltic pump component 301. The curvilinear guiding segment 323 supports the peristaltic tube 308 to stay in contact with the outer surface of at least a couple of rollers (not shown), which are received within the circular area 325 of the peristaltic pump component 301, so that the peristaltic tube 308 is sequentially squeezed by the rollers against the internal wall of the curvilinear guiding segment 323 for suitably advancing the fluid along the peristaltic tube during operation of the peristaltic pump. Typically, the second rectilinear guiding segment 324 houses a connector for assembling together the peristaltic tube 308 and the delivery tube 305, depending on the specific technical solution that is envisaged, as it will be better explained in the following of the present disclosure.

According to the prior art, as better represented in FIG. 5, the longitudinal axis X-X of the inlet port 311 is substantially perpendicular to the longitudinal axis Y-Y of the guiding path proximal extremity, i.e. the proximal end of the curved guiding segment 321 that is in direct fluid communication with the distal end of the inlet connector 304. This means that the fluid entering the peristaltic pump component 301 through the inlet port 311 (see arrow A of FIG. 5) initially flows (inside the proximal end of the inlet connector 304) in a direction that is substantially parallel to said longitudinal axis X-X, but then it is suddenly forced to turn of about 90° in order to access the distal end of the inlet connector 304 and then to enter the peristaltic tube 308, thereby following a direction that is substantially parallel to said longitudinal axis Y-Y.

The Applicant has noticed that said sudden change in direction of the fluid flow while entering the peristaltic pump component 301 (i.e. immediately after having crossed the inlet port 311) causes fluid flow disturbances (turbulences) and recirculation which may negatively impact the peristaltic pump performances, especially when very demanding high hydraulic performances are needed due to the presence of already inserted medical devices, such as PICCs & PORTs. Therefore, in order to improve the hydraulic performance of a syringe-less injection system, the Applicant has perceived the need of optimizing the path of the fluid flowing into the patient set assembly of the injection system.

Figure 6:
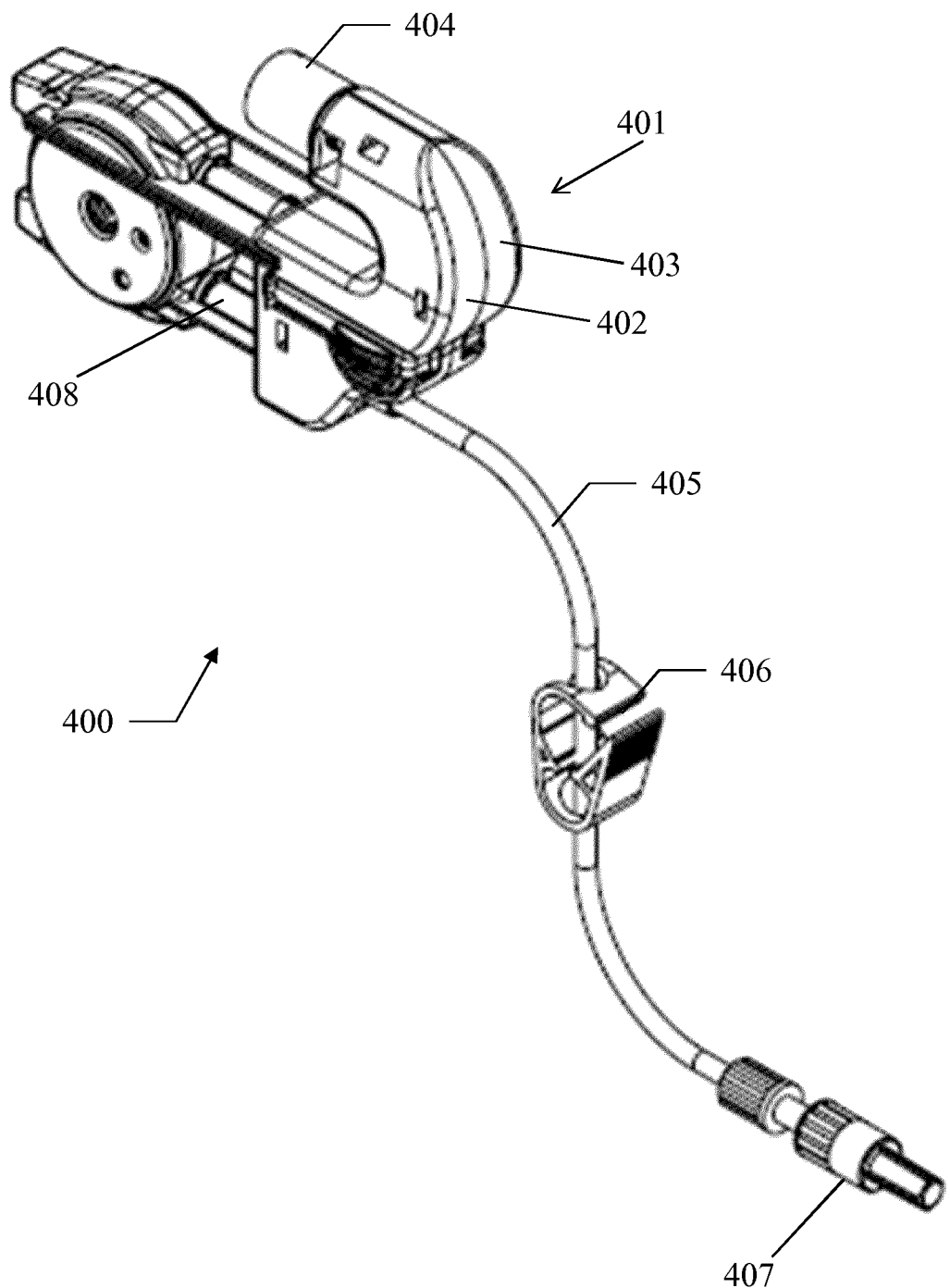
FIG. 6 shows a pictorial perspective view of a patient set assembly according to an embodiment of the present disclosure.

FIG. 6 shows a perspective view of a patient set assembly 400 according to an embodiment of the present disclosure. The patient set assembly 400 comprises a peristaltic pump component 401 and a delivery tube 405, the latter being provided at its distal end with a connection element 407 for fluidically communicate with a patient line (not shown) or directly with a peripheral catheter (not shown) inserted within a patient's vein or artery. The delivery tube 405 is typically provided also with a clip 406 for pinching the tube and closing the delivery line during positioning of the peripheral catheter.

Figure 9:
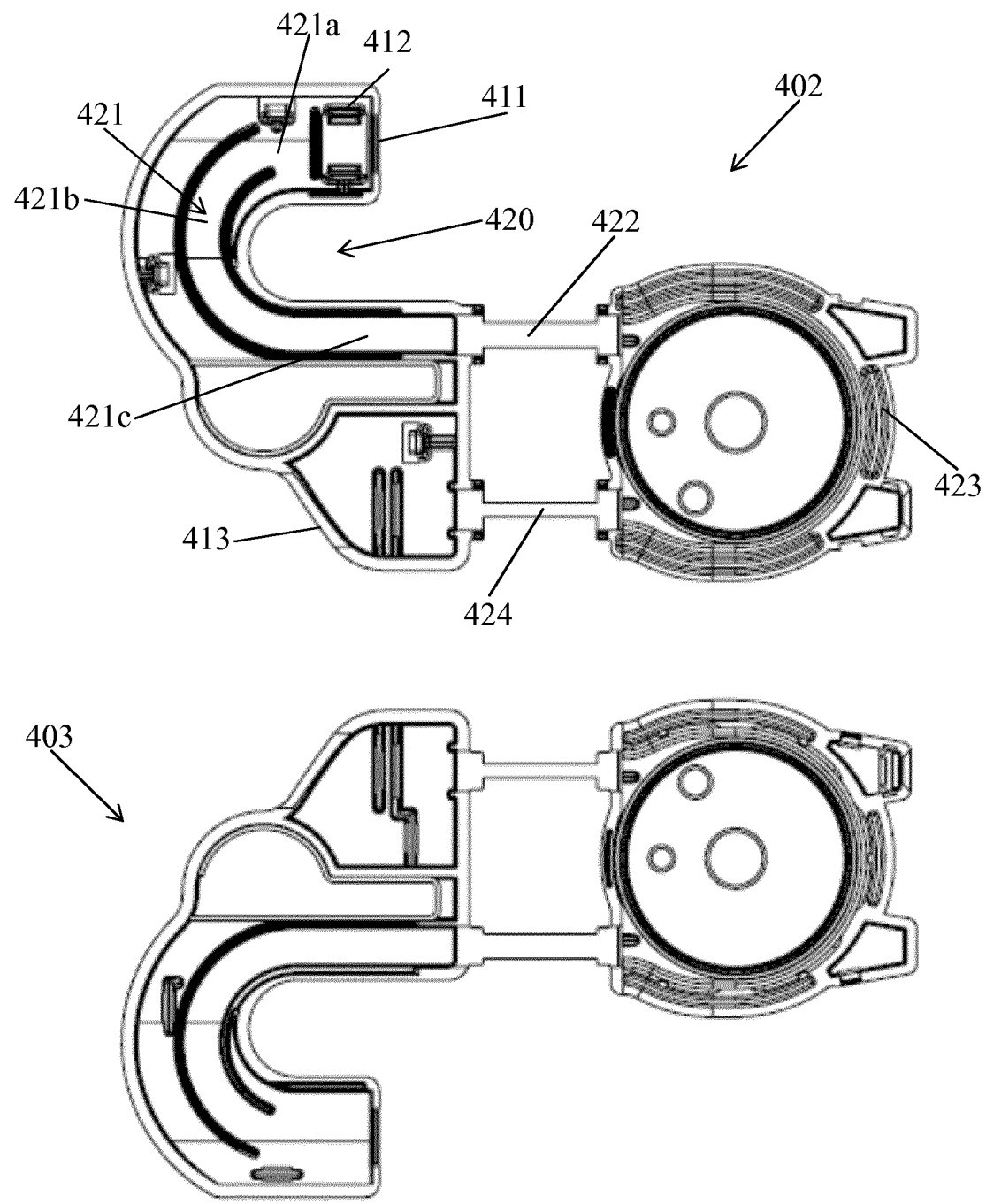
FIG. 9 shows a top plan view respectively of the first half and of the second half of the casing of the peristaltic pump component of FIG. 7.

As better shown in FIG. 9, the peristaltic pump component 401 comprises two specular mating parts 402, 403 which, once assembled together (e.g. preferably by gluing or by welding), define a closed casing for receiving an inlet connector 404 and at least a couple of rollers 450 (shown in FIG. 10) of the peristaltic pump. The two mating parts 402, 403 also define a guiding path 420 for suitably guiding a peristaltic tube 408 fluidically communicating, respectively, with the inlet connector 404 and the delivery tube 405.

Figure 7:
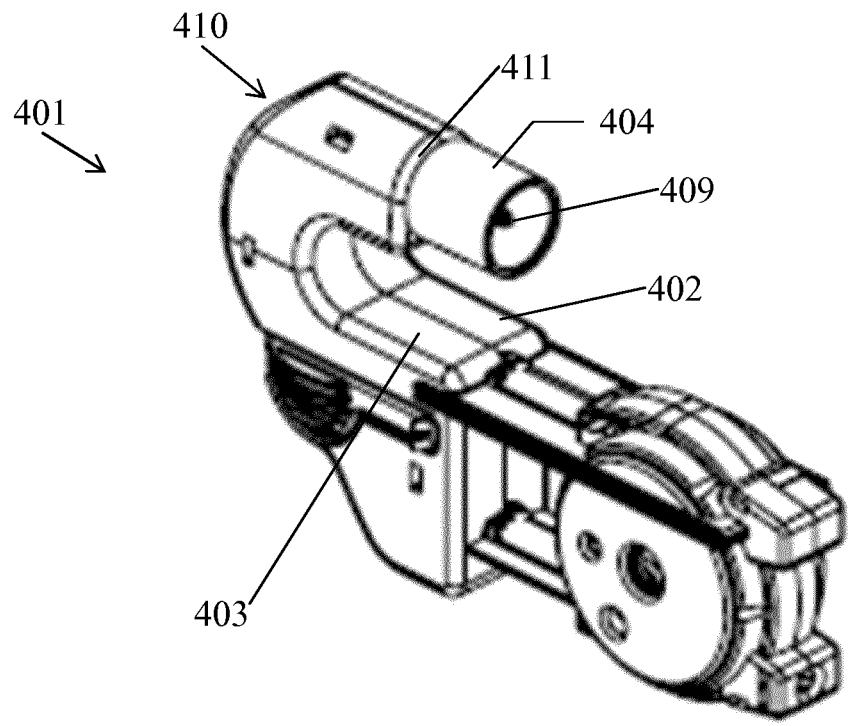
FIG. 7 shows a pictorial perspective view of a peristaltic pump component of the patient set assembly of FIG. 6.

According to the embodiment shown in FIG. 7, the inlet connector 404 is a spike connector comprising a spike 409 which, during operation of the injection system 100, penetrates a membrane (septum) possessed by the T-connector 144 of the delivery arrangement 135, thereby making the fluid connection between the delivery arrangement 135 and the patient set assembly 400. The inlet connector 404 is positioned in correspondence of an inlet port 411 of the peristaltic pump component 401 so that the inlet connector proximal end (i.e. the inlet connector portion provided with the spike 409) protrudes away from the inlet port 411.

According to an embodiment of the present disclosure, the casing of the peristaltic pump component 401 comprises a protruding portion 410 which contributes in defining a substantially U-shaped extension of the casing. In other words, according to the present disclosure, in proximity of the inlet port 411, the casing of the peristaltic pump component 401 has a substantially U-shaped configuration for an improved accommodation of the inlet connector 404 and of the peristaltic tube 408 as better explained in the following of the present description.

According to the present disclosure the inlet connector 404 is a straight-type connector and clipping members 412 are provided within the protruding portion 410, in proximity of the inlet port 411, for properly and safely engaging and retaining the inlet connector 404 within the casing of the peristaltic pump component 401.

Figure 8:
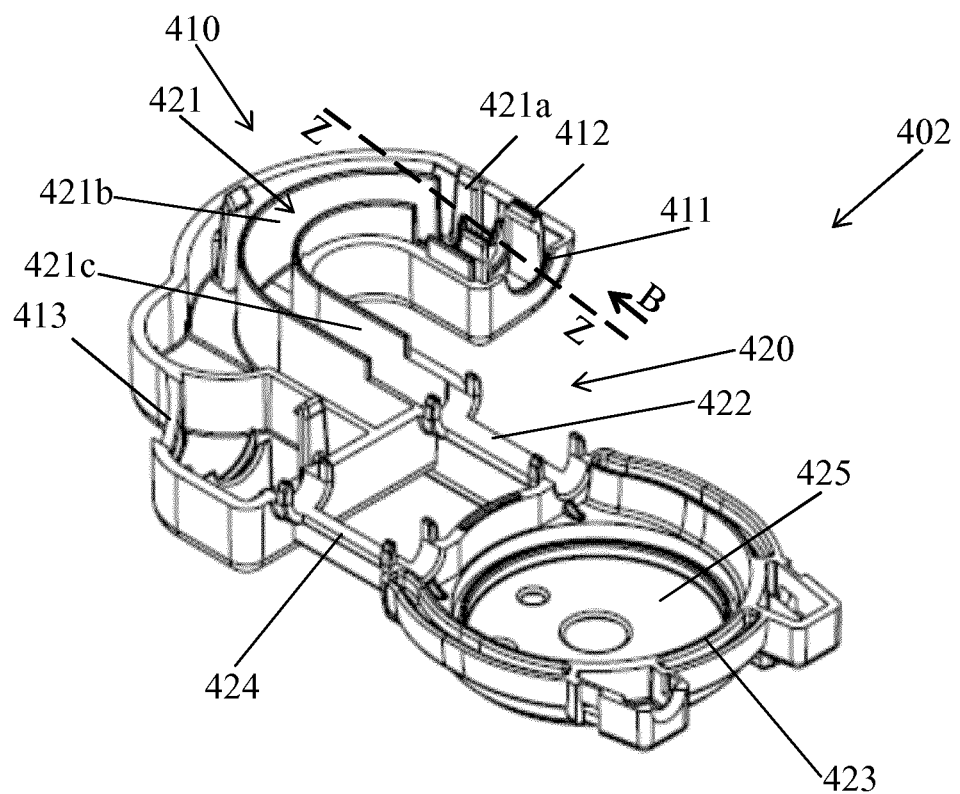
FIG. 8 shows a pictorial perspective view of one half of the casing of the peristaltic pump component of FIG. 7.
Figure 10:
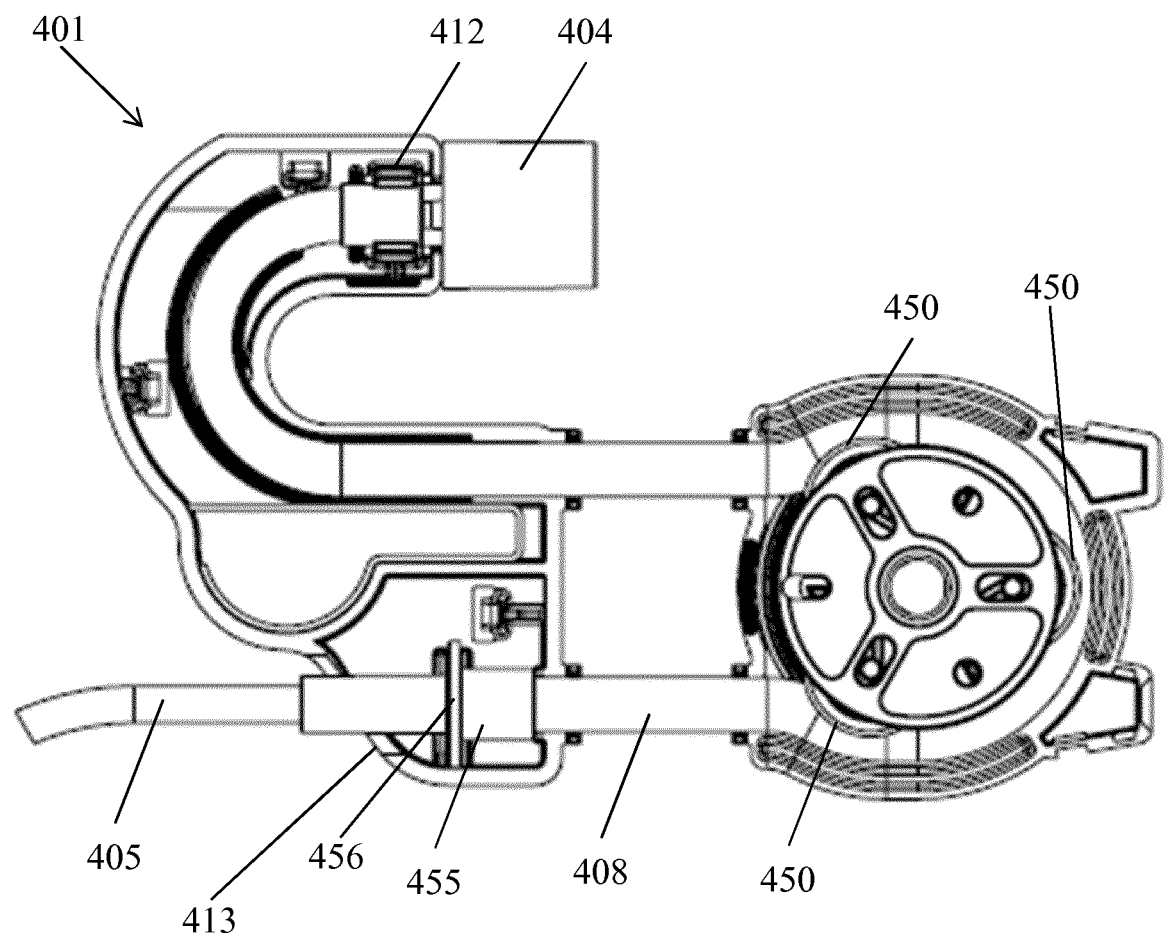
FIG. 10 shows a top plan view of a partial patient set assembly in which one half of the casing of the peristaltic pump component has been removed for clarity.

As shown in detail in FIGS. 8 to 10, the guiding path 420 comprises a plurality of guiding segments for housing and guiding the peristaltic tube 408 from the inlet connector 404, along the rollers 450 (shown in FIG. 10) of the peristaltic pump component 401 and finally up to the exit port 413 thereof. FIG. 8 shows a perspective view of only the first mating part 402 of the peristaltic pump component 401, while FIG. 9 shows a plan top view of both mating parts 402, 403 within which the guiding path 420 is suitably designed and defined.

In detail, the guiding path 420 comprises a substantially U-shaped guiding segment 421 which is mainly obtained inside the protruding portion 410 and which guides the peristaltic tube 408 to the distal end of the inlet connector 404. More precisely, the substantially U-shaped guiding segment 421 is contained in the protruding portion 410 for the majority of its extension while only a small portion of the substantially U-shaped guiding segment 421 is received within the rectangular portion of the casing of the peristaltic pump component 401. In more detail, the substantially U-shaped guiding segment 421 comprises a first straight branch 421a positioned in proximity of the clipping members 412 for retaining the inlet connector 404, a curved segment 421b connected to the first straight branch 421a and whose curvature substantially corresponds and matches the curvature of the protrusion portion 410, and a second straight branch 421c connected to the curved segment 421b.

Moving in the direction towards the exit port 413, the guiding path 420 further and successively comprises a first rectilinear guiding segment 422, a curvilinear guiding segment 423 and a second rectilinear guiding segment 424, these segments being all contained in the substantially rectangular portion of the casing of the peristaltic pump component 401. The curvilinear guiding segment 423 supports the peristaltic tube 408 to stay in contact with the outer surface of at least a couple of rollers 450 (three rollers 450 being shown in FIG. 10), which are received within the circular area 425 of the peristaltic pump component 301, so that the peristaltic tube 408 is sequentially squeezed by the rollers against the internal wall of the curvilinear guiding segment 423 for suitably advancing the fluid along the peristaltic tube during operation of the peristaltic pump. Typically, the second rectilinear guiding segment 424 houses a connector for assembling together the peristaltic tube 408 and the delivery tube 405, depending on the specific technical solution that is envisaged, as it will be better explained in the following of the present disclosure.

According to the present disclosure, as better represented in FIG. 8, the longitudinal axis Z-Z of the inlet port 411 is substantially parallel to (if not even coinciding with) the longitudinal axis of the inlet connector 404 (which is a straight-type connector) and to the longitudinal axis of the first straight branch 421a of the substantially U-shaped guiding segment 421 that is in direct fluid communication with the inlet connector 404.

In comparison with the prior art solution described with reference to FIG. 5 (for instance), the Applicant has found that the U-shaped configuration of the protruding portion 410 (and thus of the corresponding U-shaped guiding segment 421) according to the present disclosure allows the fluid entering the peristaltic pump component 401 through the inlet port 411 (see arrow B of FIG. 8) to regularly and smoothly flow into the inlet connector 404 and then into the peristaltic tube 408 (housed within the guiding path 420) with substantially no occurrence of undesired turbulent phenomena, thereby improving the injection system overall hydraulic performance.

Moreover, the Applicant has also found that the solution according to the present disclosure is particularly advantageous since the tolerances in size of the peristaltic tube (in particular the tolerances of the peristaltic tube length) can be less severe and less strict thanks to the U-shaped guiding segment 421 of the guiding path 420. In fact, the U-shaped portion of the guiding path allows to suitably arrange peristaltic tubes which can be shorter or longer than the predetermined tolerance ranges. This aspect is particularly relevant since it considerably reduces the design constraints which are requested to be met by the tube manufacturers.

Furthermore, the Applicant has found that the solution according to the present disclosure is particularly advantageous also in terms of ergonomics and easiness of use during operation of the injection system. In fact, the presence of the substantially U-shaped protruding portion 410 of the peristaltic pump component 401 according to the present disclosure has sensibly increased the overall size thereof, especially in correspondence of the area that is used by the operator to manipulate the peristaltic pump component 401, i.e. mainly to load and unload the latter into/from the pressurizing unit 140 of the injection system 100. The increased area can be well appreciated by the operator, in particular when the peristaltic pump component 401 has to be disengaged from the pressurizing unit 140. In fact, in this particular condition, most part of the peristaltic pump component 401 resides internally to the injector head and typically only a small portion of the peristaltic pump component 401 is available to the operator for grabbing it and discharging the patient set assembly. On the contrary, thanks to the solution of the present disclosure, during operation a major part of the substantially U-shaped protruding portion 410 protrudes out from the pressurizing unit 140 and the operator can easily access and grab the peristaltic pump component 401 for disengagement thereof.

According to an embodiment of the present disclosure (as represented in FIG. 10), the peristaltic tube 408 is connected to the delivery tube 405 by means of a connector 455 which is safely and properly positioned within the peristaltic pump component 401 in proximity of the exit port 413. The connector 455 is suitably kept in place and correctly positioned within the peristaltic pump component 401 by means of an additional clipping member 456.

According to an embodiment of the present disclosure, the internal diameter of the delivery tube 405 is selected to be lower than the internal diameter of the peristaltic tube 408. According to an alternative embodiment of the present disclosure, in order to further improve the hydraulic performance of the injection system 100, the delivery tube 405 and the peristaltic tube 408 are selected to have the same internal diameter so that any tube cross-section restriction is substantially avoided when the fluid flows from the peristaltic tube into the delivery tube and no drop pressure will occur.

According to an embodiment of the present disclosure, in order to further improve the hydraulic performance of the injection system 100, the delivery tube 405 is selected to have a hardness value higher than the hardness value of the peristaltic tube 408 in order to avoid blowing of the tube as a consequence of the pressure increase.

According to an alternative embodiment of the present disclosure (not shown in the figures), the delivery tube 405 is cut to be very short and a connection element is provided at its distal end so that a more versatile solution is provided. In fact, the connection element (e.g. a Luer connector) can be used for connecting a patient line that, based on the applicable law and regulatory rules of each specific country, can be of the single-use (i.e. for a single patient only) or of the multi-use (i.e. for multiple patients) type. This versatile solution is particularly advantageous since said patient set assembly can be easily adapted to and satisfy very specific needs on a case by case basis. For example, if a child or a baby is requested to be injected, a particularly tiny delivery tube would be associated to the connection element of the patient set assembly; on the contrary, for cardiac applications typically a bigger delivery tube is needed and thus would be associated to the connection element of the patient set assembly. Therefore, it is apparent that the patient set assembly according to such versatile solution can be considered as a standard component which can be used in any application, while only the distal portion of the delivery tube will be changed and selected on the basis of the very specific application/patient needs or requirements.

According to a further alternative embodiment of the present disclosure (not shown in the figures), the peristaltic tube 408 and the delivery tube 405 are exactly the same tube, thereby resulting in a less complex and less expensive patient set assembly 400.

Preferably, the peristaltic tube 408 is made from polyurethane since this material can be pretty easily deformed by the rollers of the peristaltic pump, but, at the same time, it also fully and quickly recovers its original shape when it is not squeezed by the rollers, thereby ensuring that the predetermined fluid volumes are properly loaded within the peristaltic tube portions enclosed between two successive rollers and then advanced along the peristaltic tube and the delivery tube.

Alternatively, the peristaltic tube 408 is a multilayer tube which favorably combines the mechanical properties of different materials for an improved overall performance of said peristaltic tube. For instance, the multilayer tube comprises an inner layer made from TPE (Thermoplastic Elastomers) and an outer layer made from polyurethane, thereby combining the above mentioned advantages of polyurethane with a good behavior with respect to aging of TPE.

Figure 11:
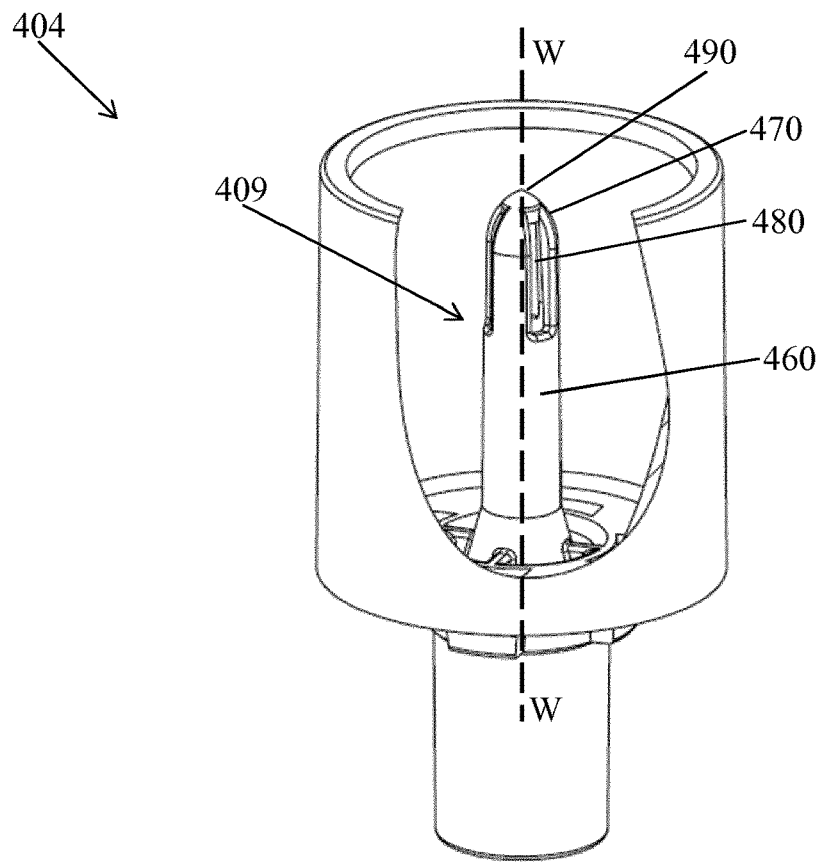
FIG. 11 and FIG. 12 show perspective views of an inlet spike connector of a patient set assembly according to an embodiment of the present disclosure.
Figure 12:
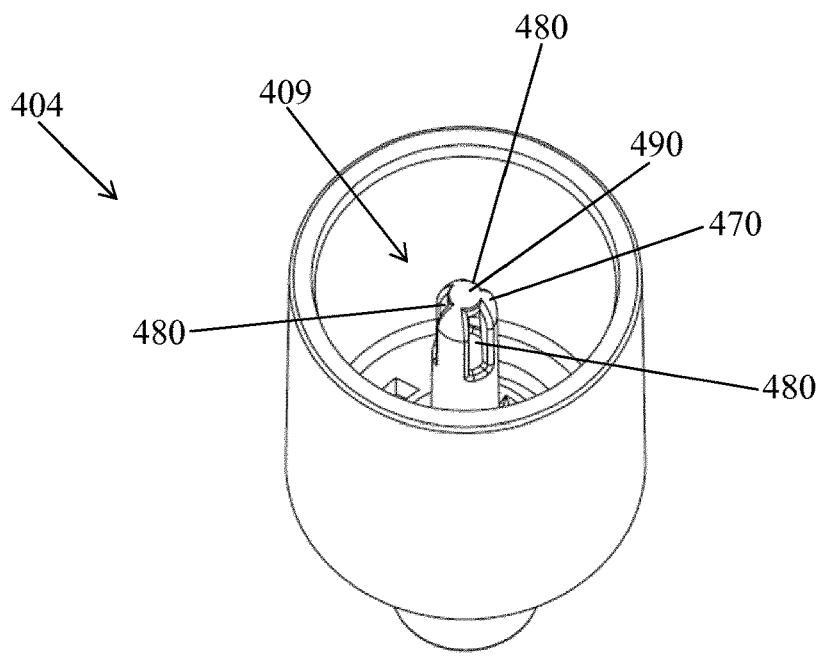

According to a further embodiment of the present disclosure, as better shown in FIGS. 11 and 12, the inlet connector 404 is a spike connector comprising a spike 409. In detail, the spike 409 comprises a cylindrical hollow shaft 460 (which defines an internal fluid passage) and a substantially rounded, cone-shaped portion 470 provided at the distal end of the shaft 460, said portion terminating in a substantially rounded and solid tip 490. The spike 409 further comprises a plurality of elongated inlet openings 480 (e.g. three openings are shown in FIG. 12) which, according to the embodiment shown in FIGS. 11 and 12, partially extend along the shaft and the substantially rounded, cone-shaped portion, said elongated inlet openings being in fluid communication with the internal fluid passage defined by the cylindrical hollow shaft 460. Since the substantially rounded, cone-shaped portion 470 is closed at its distal tip 490, the fluid can enter the spike 409 only through the elongated inlet openings 480. According to the embodiment shown in the figures, said elongated inlet openings 480 have a substantially rectangular shape and their longitudinal extension is substantially parallel to the spike longitudinal axis W-W, at least for the part of the elongated inlet opening that extends along the spike cylindrical shaft. Moreover, in order to homogeneously distribute the fluid flow into the internal cavity of the spike 409, the elongated inlet openings are circumferentially arranged to be equally distanced from each other along the lateral surface of the cylindrical hollow shaft 460, and their distribution as well as their configuration is suitably designed for increasing the maximum area available for the fluid passage. Therefore, the implementation of laterally and circumferentially arranged elongated inlet openings (instead of one central opening) favorably improves the fluid inflow into the inlet connector 404. Furthermore, the substantially rounded, cone-shaped portion 470 at the distal tip 490 of the spike 409 has been designed for improving the penetration efficacy of the spike through the membrane (septum) possessed by the T-connector 144 of the delivery arrangement 135. In fact, the Applicant has perceived the need of providing a spike design which can contribute not only in promoting a correct and important fluid flow through the spike, but also in guaranteeing a gradual and efficient penetration of the spike into the T-connector membrane in order to preserve the integrity thereof after multiple spike insertions, especially taking into consideration that the delivery arrangement ("Day Set") is designed to remain in operation for a whole working day. Finally, the substantially rounded, cone-shaped portion 470 of the spike 409 has also the advantage of facilitating the operator during the insertion of the spike 409 through the membrane (septum) of the T-connector 144 (that is provided with a suitable cut at its central portion for better guiding and facilitating the spike insertion) since the spike end rounded surface encounters less resistance to penetration in comparison with a cylindrical hollow spike that is traditionally possessed by the spike connectors 304 of current patient set assemblies 300.

Therefore, according to one embodiment of the present disclosure, the patient set assembly 400 comprises at least one improved inlet connector 404 provided with the new modified spike 409.

According to a further embodiment of the present disclosure, the patient set assembly 300 comprises at least one improved inlet connector 404 provided with the new modified spike 409.

According to a further embodiment of the present disclosure, the delivery arrangement 135 comprises at least one improved inlet connector 404 provided with the new modified spike 409. According to this embodiment, the connection elements 143a, 143b of FIG. 1 and FIG. 2 are substituted with the improved inlet connectors 404, whose spikes 409 penetrate a septum (membrane) possessed by corresponding bottle connectors 130a, 130b.

In operation, for each injection to be performed, the operator positions the injection system 100 close to the patient to be examined and then turns the injection system on. If not already done, the operator installs the delivery arrangement 135 by inserting each drip chamber 142a, 142b and each connection element 143a, 143b into the corresponding bottle holder 115a, 115b, thereby releasably blocking them therein (for example, by means of a snap-fit mechanism). When the pouch 110c (containing the saline solution) is not installed, the control unit 155 displays a message on its screen prompting the operator to do so. If the pouch 110c is to be used, the operator pierces a seal of the pouch 110c with the spike 143c, hangs the pouch 110c from the hook 125c and fills the reservoir 142c completely with the saline solution (by repeatedly squeezing it). At this point, the operator programs the control unit 155 (either at the control unit 155 or at an injector remote console not shown in the figures) by entering specific information relating to the saline solution of the pouch 110c (for example, its brand name and volume). Otherwise, if the pouch 110c is not used, the operator enters a corresponding command to the control unit 155 (or the remote console). In both cases, when the bottle 110a (with the contrast agent) is not installed, the control unit 155 displays a message on its screen prompting the operator to do so. In response thereto, the operator generally takes the bottle 110a from a separate warmer (not shown in the figures), wherein the bottle 110a has been pre-warmed to a target temperature. The target temperature is typically set to a value high enough to allow injecting the contrast agent efficiently (for example, at the desired flow rate) and comfortably for the patient, but not too high to be harmful for the patient. Typically the target temperature is in a range from 32° C. to 37.5° C. Alternatively, this procedure is not performed and thus the contrast agent is not pre-warmed being injected at room temperature. The operator pierces a seal of the bottle 110a with the spike of the bottle connector 130a. Then he turns the bottle 110a (with the bottle connector 130a connected thereto) up-side-down, he inserts the bottle connector 130a into the connection port 132a (so as to connect its connection element to the connection element 143a), he mounts the protective cover 120a on the bottle holder 115a (so as to protect and thermally insulate the bottle 110a) and then he fills the drip chamber 142a with the contrast agent (by repeatedly manually squeezing the reservoir 142a). At this point, the operator programs the control unit 155 (either at the control unit 155 or at the injector remote console) by entering specific information relating to the contrast agent of the bottle 110a (for example, its brand name and volume). The operator repeats the same operations, if necessary, to install the other bottle 110b (which may contain the same contrast agent of bottle 110a or a different contrast agent or even a saline solution). The control unit 155 then displays a message on its screen prompting the operator to install the patient set assembly 400. Therefore the operator can introduce the peristaltic pump component 401 into the dedicated slot of the pressurizing unit 140, connect the peristaltic pump component 401 to the T-connector 144 and arm the injector which will be ready to run a predetermined selected injection procedure.

In case the patient set assembly 400 is for multiple use (as shown in FIG. 2), the operator further connects the connection element 501 of the additional patient line 500 to the connection element 407 of the delivery tube 405.

Successively the operator separately primes each transfer line 141a, 141b and 141c by selecting a corresponding priming function on the control unit 155 (or at the remote console), so as to eliminate air bubbles that are possibly present within the transfer lines 141a, 141b and 141c, the delivery tube 405 and/or the (possible) additional patient line 500. Alternatively and preferably, the priming phase is advantageously automatically performed by the injection system without the need for the operator to execute it manually. Once this priming phase has been terminated (and no air is sensed in the injection system 100), the operator finally connects the connection element 407 of the patient set assembly 400 (in case the patient set assembly is for a single use) or the connection element 502 of the additional patient line 500 (in case the patient set assembly is for multiple use) to the connection element of a peripheral catheter (not shown in the figures) which has already been inserted into the patient's vasculature.

Then the operator programs the control unit 155 (or the remote console) by entering or selecting information related to the injection examination to be performed (for example, the needle gauge of the peripheral catheter, the injection protocol comprising one or more injection phases, each injection phase being defined by the type, volume and flow rate of the medical fluids to be injected, possibly selected among pre-defined injection protocols for different types of injection procedures and correlated scan examinations).

The injection protocol (i.e. the number of injection phases, the sequence of injection phases, the injection parameters like flow rate and duration time, contrast agent and saline details, needle gauge) specific for a given patient to be examined can be manually introduced by the operator through the control unit 155 (or the remote console). Alternatively, the operator can download a desired injection protocol from a removable memory, such as a USB flash drive. Alternatively, the operator can download a desired injection protocol, as well as the relevant data of the patient to be examined, from a server which can connect more than one injection system 100 and, in case, also a plurality of clinical premises.

Finally the operator can start the scan examination which combines the functionalities of the injection system with the functionalities of the imaging device, the latter being operated in conjunction with the injection system that provides for the contrast agent activity which is used during the scan procedure. At the end of the scan examination, the injection system 100 stops automatically and the operator disconnects the patient set assembly 400 or the additional patient line 500 from the peripheral catheter.

As mentioned above, if the patient set assembly 400 is of the single-use type, the operator disengages the peristaltic pump component 401 and he discards the used patient set assembly 400. On the contrary, if the patient set assembly 400 is of the multiple-use type and its usage time (typically 12 hrs) has not elapsed yet, the operator keeps the peristaltic pump component 401—and the peristaltic tube 408 as well as the delivery tube 405 loaded therein—within the pressurizing unit 140 and he finally removes and discards only the used additional patient line 500. At this point the injection procedure of the examined patient can be considered completed.

As mentioned above, if the delivery arrangement 135 is a disposable element that is required to be changed every 24 hours, at the end of the injection procedure the delivery arrangement 135 is not discarded if its usage time has not elapsed yet, and it remains installed on the injector, ready for a new patient to be injected and a new injection procedure to be started.

The injection system 100 of FIG. 1 and FIG. 2 comprises three separate supply stations 105a, 105, 105c. However, the present disclosure can be applied to an injection system that is provided with a single supply station (not shown). Analogously, the present disclosure can be applied to an injection system that is provided with two separate supply stations (not shown).

MODIFICATIONS

In order to satisfy local and specific requirements, a person skilled in the art may apply many logical and/or physical modifications and alterations to the present disclosure. More specifically, although this disclosure has been described with a certain degree of particularity with reference to one or more embodiments thereof, it should be understood that various omissions, substitutions and changes in the form and details as well as other embodiments are possible. Particularly, different embodiments of the present disclosure may even be practiced without the specific details (such as the numerical values) set forth in the preceding description to provide a more thorough understanding thereof. Conversely, well-known features may have been omitted or simplified in order not to obscure the description with unnecessary particulars. Moreover, it is expressly intended that specific elements and/or method steps described in connection with any embodiment of the present disclosure may be incorporated in any other embodiment as a matter of general design choice. In any case, each numerical value should be read as modified by the term about (unless already done) and each range of numerical values should be intended as expressly specifying any possible number along the continuum within the range (comprising its end points). Moreover, ordinal or other qualifiers are merely used as labels to distinguish elements with the same name but do not by themselves connote any priority, precedence or order. The terms include, comprise, have, contain and involve (and any forms thereof) should be intended with an open, non-exhaustive meaning (i.e., not limited to the recited items), the terms based on, dependent on, according to, function of (and any forms thereof) should be intended as a non-exclusive relationship (i.e., with possible further variables involved), the term a/an should be intended as one or more items (unless expressly indicated otherwise), and the term means for (or any means-plus-function formulation) should be intended as any structure adapted or configured for carrying out the relevant function.

In an embodiment, the injection system is for injecting one or more fluids into a patient. However, the fluids may be in any number and of any type (for example, whatever medical fluid to be used in a generic medical application for diagnostic or therapeutic purposes, such as a drug or a body fluid, or more generally to be used in any other treatment, such as for cosmetic purposes); moreover, the fluid may be injected in any way (for example, intra-arterially) into any (human or animal) patient.

In an embodiment, the injection system comprises one or more supply stations each one for supplying one of the fluids to be injected. However, the injection system may comprise any number of supply stations (down to a single one) for supplying the same or different fluids (in any combination).

In an embodiment, the injection system is for injecting the fluids into the patient during a scan examination thereof; the fluids are one or more medical fluids comprising a contrast agent and/or a saline solution. However, the injection system may be used for any scan examination (for example, in MR, nuclear or ultrasound imaging applications); moreover, the injection system may be used with any contrast agent (for example, a barium-based contrast agent such as barium sulfate, gadolinium, a radioisotope, a suspension of gas-filled microbubbles), any saline solution (for example, with the addition of dextrose), any combination thereof or more generally with any medical fluid(s).

The invention claimed is:

1. An injection system (100) comprising:
    at least one supply station (105a; 105b; 105c) for supplying a fluid to be injected into a patient's vasculature;
    a pressurizing unit (140) comprising a motor for pressurizing the fluid received from said at least one supply station;
    a delivery arrangement (135) in fluid communication with said at least one supply station;
    a patient set assembly (400) in fluid communication with said delivery arrangement, said patient set assembly comprising:
        a delivery tube (405) for delivering the pressurized fluid to the patient, and
        a peristaltic pump component (401) comprising a casing (402, 403), wherein the casing comprises an inlet port (411) and an exit port (413), the inlet port being in fluid communication with the delivery arrangement, and the exit port being in fluid communication with the delivery tube,
    characterized in that, the casing (402, 403) defines a guiding path (420) when closed and a portion of the guiding path (420) in proximity of said inlet port has a substantially U-shaped configuration.

2. The injection system (100) according to claim 1, characterized in that the peristaltic pump component (401) comprises two specular mating parts (402, 403) which, once assembled together, define said casing.

3. The injection system (100) according to claim 1, characterized in that said casing is closed and houses therein an inlet connector (404), at least a couple of rollers (450) of the peristaltic pump component (401) and a guiding path (420) for guiding a peristaltic tube (408) in fluid communication respectively with the inlet connector (404) and the delivery tube (405).

4. The injection system (100) according to claim 1, characterized in that said casing further comprises a protruding portion (410) which contributes in defining said substantially U-shaped configuration in proximity of said inlet port.

5. The injection system (100) according to claim 4, characterized in that the guiding path (420) comprises a substantially U-shaped guiding segment (421) which, for the majority of its extension, is mainly positioned within the protruding portion (410).

6. The injection system (100) according to claim 5, characterized in that the substantially U-shaped guiding segment (421) comprises a first straight branch (421a) positioned in proximity of clipping members (412) for retaining the inlet connector (404), a curved segment (421b) connected to the first straight branch (421a) and whose curvature corresponds to the curvature of the protrusion portion (410), and a second straight branch (421c) connected to the curved segment (421b).

7. The injection system (100) according to claim 3, characterized in that, moving in the direction towards the exit port (413), the guiding path (420) further comprises a first rectilinear guiding segment (422), a curvilinear guiding segment (423) and a second rectilinear guiding segment (424), said segments being all contained in a substantially rectangular portion of said casing.

8. The injection system (100) according to claim 6, characterized in that a longitudinal axis (Z-Z) of the inlet port (411) is substantially parallel to a longitudinal axis of the inlet connector (404) and to a longitudinal axis of the first straight branch (421a) that is in direct fluid communication with the inlet connector (404).

9. The injection system (100) according to claim 1, characterized in that the delivery tube (405) is cut to be very short and a connection element is provided at a distal end of said delivery tube.

10. A patient set assembly (400) for delivering a pressurized fluid to a patient, the patient set assembly comprising:
  a delivery tube (405) in fluid communication with the patient, and
  a peristaltic pump component (401) comprising:
    a casing (402, 403) comprising an inlet port (411) and an exit port (413), the inlet port being in fluid communication with a delivery arrangement (135) of an injection system (100) and the exit port being in fluid communication with the delivery tube;
    an inlet connector (404) for connecting said peristaltic pump component to a connector (144) of the delivery arrangement (135), said inlet connector being arranged at said inlet port, and
    at least a couple of rollers (450) for engaging a peristaltic tube (408) in fluid communication with said inlet connector and for pressurizing the fluid flowing into the peristaltic tube when the peristaltic pump component is connected to a pressurizing unit (140) of the injection system and the pressurizing unit is operating,
  characterized in that, the casing (402, 403) defines a guiding path (420) when closed and a portion of the guiding path (420) in proximity of said inlet port has a substantially U-shaped configuration.

11. The patient set assembly according to claim 10, characterized in that a longitudinal axis (Z-Z) of the inlet port (411) is substantially parallel to a longitudinal axis of the peristaltic tube (408) at the connection area between the inlet connector (404) and the peristaltic tube.

12. The patient set assembly (400) according to claim 10, characterized in that said guiding path (420) is capable of guiding the peristaltic tube (408) in fluid communication respectively with the inlet connector (404) and the delivery tube (405).

13. The patient set assembly (400) according to claim 10, characterized in that the delivery tube (405) is cut to be very short and a connection element is provided at a distal end of said delivery tube.

14. A peristaltic pump component (401) for delivering a pressurized fluid comprising:
  a casing (402, 403) comprising an inlet port (411) and an exit port (413);
  an inlet connector (404) for connecting said peristaltic pump component to a delivery arrangement (135) of an injection system (100), said inlet connector being arranged at said inlet port, and
  at least a couple of rollers (450) for engaging a peristaltic tube (408) in fluid communication with said inlet connector and for pressurizing the fluid flowing into the peristaltic tube when the peristaltic pump component is connected to a pressurizing unit (140) of the injection system (100) and the pressurizing unit is operating,
characterized in that, the casing (402, 403) defines a guiding path (420) when closed and a portion of the guiding path (420) in proximity of said inlet port has a substantially U-shaped configuration.

15. The peristaltic pump component (401) according to claim 14, characterized in that said casing (402, 403) further comprises a protruding portion (410) which contributes in defining said substantially U-shaped configuration in proximity of said inlet port.

16. The peristaltic pump component (401) according to claim 14, wherein the guiding path (420) is capable of guiding the peristaltic tube (408) in fluid communication with the inlet connector (404).

17. The peristaltic pump component (401) according to claim 15, characterized in that the guiding path (420) comprises a substantially U-shaped guiding segment (421) which includes a curved segment (421b) whose curvature substantially corresponds and matches the curvature of the protruding portion (410).

18. The peristaltic pump component (401) according to claim 14, characterized in that the delivery tube (405) is cut to be very short and a connection element is provided at a distal end of said delivery tube.

* * * * *